US00PP28339P3

(12) United States Plant Patent
Bradford et al.

(10) Patent No.: US PP28,339 P3
(45) Date of Patent: Aug. 29, 2017

(54) PEACH TREE NAMED 'RED PRINCESS III'

(50) Latin Name: *Prunus persica*
Varietal Denomination: Red Princess III

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 54 days.

(21) Appl. No.: 14/757,242

(22) Filed: Dec. 11, 2015

(65) Prior Publication Data

US 2017/0172033 P1 Jun. 15, 2017

(51) Int. Cl.
*A01H 5/08* (2006.01)

(52) U.S. Cl.
USPC ..... Plt./197

(58) Field of Classification Search
USPC ..... Plt./197
See application file for complete search history.

(56) References Cited

U.S. PATENT DOCUMENTS

PP14,695 P2 4/2004 Bradford
PP23,530 P3 4/2013 Bradford

*Primary Examiner* — June Hwu

(57) ABSTRACT

The present invention relates to a new and distinct variety of peach tree, *Prunus persica*, broadly characterized by a large size, vigorous, hardy, self-fertile, productive and regular bearing tree. The variety blooms during the early to mid season and requires about 500 chilling hours. The fruit matures under the ecological conditions described in the latter part of May, with first picking on May 23, 2015. The fruit is uniform, large in size, acidic with traditional peach flavor, globose to slightly oblate in shape, clingstone in type, non-melting in texture, yellow in flesh color, virtually full red in skin color, and has a bitter tasting kernel.

1 Drawing Sheet

Botanical classification: *Prunus persica.*

Variety denomination: 'RED PRINCESS III'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'Red Princess III'.

In 2005 we made a first generation hybridization using 'Bright Princess' (U.S. Plant Pat. No. 14,695) peach as the selected seed parent and '7P1' (unpatented) yellow flesh peach as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2009 we selected the present variety as a single tree from the group of seedlings described above. Subsequent to origination of the present variety of peach tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Bright Princess' (U.S. Plant Pat. No. 14,695) peach, by being self-fertile, by having a large blossom, by having reniform leaf glands, and by producing peaches that are mostly red in skin color, yellow in flesh color, and globose in shape, but is quite distinguished from it by producing peaches that are non-melting instead of melting in texture, that have a bitter instead of sweet kernel, and that ripen about eighteen days earlier.

While the present variety is similar to its pollen parent, '7P1' (unpatented) peach, by being self-fertile and by producing fruit that is mostly red in skin color, yellow in flesh color, clingstone in type, and globose in shape, but is quite distinguished from it by producing fruit that is much larger in size, that is much firmer in texture, and that matures about eighteen days later.

The present variety is most similar to 'June Time' (U.S. Plant Pat. No. 23,530) peach by being vigorous, by having a large tree, by having reniform leaf glands, by being self-fertile, by having large blossoms, and by producing fruit that is nearly globose in shape, nearly full red in skin color, yellow in flesh color, large in size, and non-melting in texture, but is distinguished therefrom by blooming earlier, by requiring less chilling hours, and by producing fruit that has a bitter instead of sweet kernel and that matures about ten days earlier.

SUMMARY OF VARIETY

In summary, the present peach variety is characterized by a large size, vigorous, hardy, self-fertile, productive and regular bearing tree. The variety blooms during the early to mid season and requires about 500 chilling hours. The fruit matures under the ecological conditions described in the latter part of May, with first picking on May 23, 2015. The fruit is uniform, large in size, acidic with traditional peach flavor, globose to slightly oblate in shape, clingstone in type, non-melting in texture, yellow in flesh color, virtually full red in skin color, and has a bitter tasting kernel.

DRAWING

The accompanying photograph consists of four whole fruits positioned to display the characteristics of the skin color and form, one sliced fruit to reveal the flesh and stone, one typical tip shoot, typical leaves, and one inset to reveal a blossom as it appears during the blooming season.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of shipping ripe on May 24, 2015, on the original tree during its tenth growing season. The blossom and flower descriptions were made the previous blooming season. All major color code designations are by reference to the Inter-Society Color Council, National Bureau of Standards. Common color names are also used occasionally.

It is to be noted that the 2015 fruit season in California was very warm during the spring and the ripening times of almost all varieties were about twenty days earlier than other years.

PARENTAGE

Seed parent: 'Bright Princess' (U.S. Plant Pat. No. 14,695) peach.

Pollen parent: '7P1' peach (unpatented).

TREE

Size: Large, reaching and maintaining a height of 12' [3.66 m.] and a spread of 15' [4.57 m.] after ten growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to a vase form.

Hardiness: Hardy with respect to central California winters.

Chilling requirement: About 500 hours.

Leaf bud burst: Medium, toward the middle of flowering.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Trunk:

*Size*.—Stocky, reaching a maximum diameter of 6" [152 mm.] after the tenth growing season.

*Texture*.—Medium.

*Bark color*.—A Light brown [57. l.Br] and Moderate yellowish brown [77. m.yBr] variegation with Strong yellowish brown [74. s.yBr] crevices present.

*Lenticels*.—Approximate Number Per Square Inch: 6. Color: Dark orange yellow [72. d.OY]. Average Size: ¼" [6.4 mm.] in length. The width is typically one fourth as much as the length. Shape: Eye-shaped.

Branches:

*Size*.—Medium, diameter of limb is 3¾" [95 mm.] measured 12" above the crotch, 2⅜" [60 mm.] measured 12" above the first fork.

*Texture*.—Smooth on first and second year wood, increasing roughness with age.

*Color*.—1st Year Wood Topside: Grayish red [19. gy.R]. 1st Year Wood Underside: Brilliant yellow green [116. brill.YG]. 2nd Year Wood: A Light grayish brown [60. l.gy.Br] and Brownish orange [54. brO] variegation.

*Lenticels*.—Number Per Square Inch: About 20 on second year wood. Color: Light yellowish brown [76. l.yBr]. Average Size: Medium, 1/32" [0.8 mm.] in length. The width is typically one fourth as much as the length. Shape: Eye-shaped.

Leaves:

*Size*.—Medium. Average Length: 5⅜" [136.5 mm.]. Average Width: 1½" [38.1 mm.].

*Arrangement*.—Alternate.

*Thickness*.—Medium.

*Form*.—Elliptical.

*Apex*.—Acuminate.

*Base*.—Acute to rounded.

*Surface*.—Smooth on both sides.

*Color*.—Dorsal Surface: Moderate olive green [125. m.OlG]. Ventral Surface: Moderate yellow green [120. m.YG].

*Red midvein*.—Absent.

*Margin*.—Finely serrate.

*Venation*.—Pinnately net veined.

*Petiole*.—Average Length: 7/16" [11.1 mm.]. Average Thickness: 1/16" [1.6 mm.]. Color: Brilliant yellow green [116. brill.YG].

*Stipules*.—Number: 2 per leaf, up to 6 per growing tip. Average Length: ⅜" [9.5 mm.]. Color: Brilliant yellow green [116. brill.YG] becoming Dark yellowish brown [78. d.yBr] with age.

*Glands*.—Number: Mostly 2 to 4 per leaf. Position: First pair is at the intersection of petiole and base of blade, the rest are on the leaf blade. Form: Reniform. Size: Medium, about 1/24" [1.1 mm.] in length, about 1/48" [0.5 mm.] in width. Color: Brilliant yellow green [116. brill.YG] becoming Moderate reddish brown [43. m.rBr] in the center with age.

*Leaf buds*.—Pointed.

Flower buds:

*Hardiness*.—Hardy, with respect to central California blooming season.

*Diameter*.—Typically ⅜" [9.5 mm.] 1 week before bloom.

*Length*.—Typically ⅝" [15.9 mm.] 1 week before bloom.

*Form*.—Not appressed.

*Surface*.—Pubescent.
*Tip color*.—Light purplish pink [249. l.pPk].

Flowers: Perfect, complete, perigynous, usually a single pistil, about thirty stamens, five sepal and petal locations alternately positioned.
*Type*.—Showy, large.
*Average flower diameter*.—2" [50.8 mm.].
*Average flower depth*.—7/16" [11.1 mm.] when fully open.
*Average pedicel length*.—1/8" [3.2 mm.].
*Number of petals*.—Mostly five, extra petal fragments occur frequently, double blossoms are occasionally observed.
*Petal shape*.—Circular to oval.
*Petal margin*.—Entire, quite wavy.
*Average petal diameter*.—13/16" [20.6 mm.].
*Average petal length*.—3/4" [19.1 mm.].
*Petal apex*.—Rounded.
*Petal base*.—Rounded to somewhat truncate.
*Petal color*.—Light pink [4. l.Pk] toward the apex, Moderate pink [5. m.Pk] toward the base on both sides.
*Anther color*.—Deep red [13. deep R] over a Light yellow [86. l.Y] center at bloom onset.
*Pollen*.—Anthers produce an abundance of Brilliant yellow [83. brill.Y] pollen.
*Stigma color*.—Pale greenish yellow [104. p.gY].
*Stigma position*.—Typically located about even with the nearby anthers.
*Ovary*.—Pubescent.
*Sepal color*.—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length*.—1/4" [6.4 mm.].
*Sepal width*.—1/4" [6.4 mm.].
*Sepal apex*.—Rounded to elliptical to match the sepal length and width.
*Sepal margin*.—Fairly smooth.
*Average pistil length*.—11/16" [17.5 mm.].
*Average stamen length*.—9/16" [14.3 mm.].
*Fragrance*.—Moderate.
*Blooming period*.—Early to medium compared to other varieties, six days before 'June Time' (U.S. Plant Pat. No. 23,530) peach.
*Onset of bloom*.—One percent on Feb. 14, 2015.
*Date of full bloom*.—Feb. 23, 2015.
*Duration of bloom*.—One to two weeks, dependent on ambient temperature.
*Bloom density*.—Medium to heavy.
*Number per cluster*.—1 to 3 with single flowers most common.

FRUIT

Maturity when described: Shipping ripe, May 24, 2015.
Date of first picking: May 23, 2015.
Date of last picking: Jun. 5, 2015.
Size: Uniform, large.
*Average diameter axially*.—2 7/8" [73.0 mm.].
*Average diameter across suture plane*.—3 1/8" [79.4 mm.].
*Average diameter across cheek plane*.—3 1/8" [79.4 mm.].
*Typical weight*.—8.8 ounces [250 grams].

Form: Uniform, globose with slight axial compression, symmetrical.
*Longitudinal section form*.—Round to oblate.
*Axial view*.—Round.

Suture: Extends from the base to the pistil point, has a slight depression beyond pistil point.
*Near the base*.—A shallow groove.
*Along the side*.—A very shallow trough.
*Near the apex*.—A shallow groove.

Ventral surface: Rounded strongly, lipped slightly toward the apex.
Lips: Equal.
Cavity: Flaring, elongated in the suture plane, suture always showing on one side, occasionally on both. Light orange yellow [70. l.OY] stem markings typical.
*Depth*.—5/8" [15.9 mm.].
*Breadth*.—1" [25.4 mm.].
Base: Truncate, slightly cordate if viewed parallel to the suture.
Apex: Rounded with about twenty percent slightly mammiform.
Pistil point: Mostly oblique, very short in length, depressed within the suture on about eighty percent.
Stem: Medium.
*Average length*.—3/8" [9.5 mm.].
*Average width*.—3/16" [4.8 mm.].
Skin:
*Thickness*.—Medium.
*Surface*.—Pubescent.
*Tenacity*.—Tenacious to the flesh.
*Astringency*.—Moderate.
*Tendency to crack*.—None observed in wet season.
*Color*.—Very dark red [17. v.d.R] variegated over a Moderate reddish orange [37. m.rO] background with a slight amount of Light orange yellow [70. l.OY] areas if sun protected by a limb or leaf.
*Down*.—Moderate, very short, does not roll up when rubbed.
Flesh:
*Color*.—Brilliant yellow [83. brill.Y] from the stone to the skin with no bleeding or flecking.
*Surface of pit cavity*.—Covered with Brilliant yellow [83. brill.Y] broken fibers when twisted away from the stone.
*Amygdalin*.—Moderate.
*Juice*.—Moderate, rich.
*Texture*.—Very firm, tough, non-melting.
*Fibers*.—Few, fine, tough.
*Ripens*.—Fairly even.
*Flavor*.—Classic peach flavor, medium acidity, moderately sweet, typically 14 brix.
*Aroma*.—Moderate.
*Eating quality*.—Very good.

STONE

Type: Clingstone.
Form: Oval.
Hilum: Very narrow, oblong.
Base: Truncate, somewhat oblique.
Apex: Obtuse.
Sides: Equal.
Tip: Almost blunt.
Surface: A few furrows along the dorsal and ventral edges, pitted throughout.

Ridges: Rounded.
External color: Moderate orange yellow [71. m.OY] when first removed.
Pit wall color when cracked: Light yellowish brown [76. l.yBr].
Cavity surface color: Moderate yellowish brown [77. m.yBr].
Average pit wall thickness: ¼" [6.4 mm.].
Average length: 1⅜" [34.9 mm.].
Average width: 1" [25.4 mm.].
Average breadth: 13/16" [20.6 mm.].
Tendency to split: None.
Kernel:
*Form*.—Oval.
*Skin color*.—Pale yellow [89. p.Y] when first removed.
*Pellicle color*.—Grayish yellow [90. gy.Y].
*Vein color*.—Light yellow [86. l.Y].
*Taste*.—Bitter.
*Viable*.—Only with embryo rescue techniques.
*Average width*.—7/16" [11.1 mm.].
*Average length*.—11/16" [17.5 mm.].
*Amygdalin*.—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to 'June Time' (U.S. Plant Pat. No. 23,530) peach by being vigorous, by having a large tree, by having reniform leaf glands, by being self-fertile, by having large blossoms, and by producing fruit that is nearly globose in shape, nearly full red in skin color, yellow in flesh color, large in size, and non-melting in texture, but is distinguished therefrom by blooming earlier, by requiring less chilling hours, and by producing fruit that has a bitter instead of sweet kernel and that matures about ten days earlier.

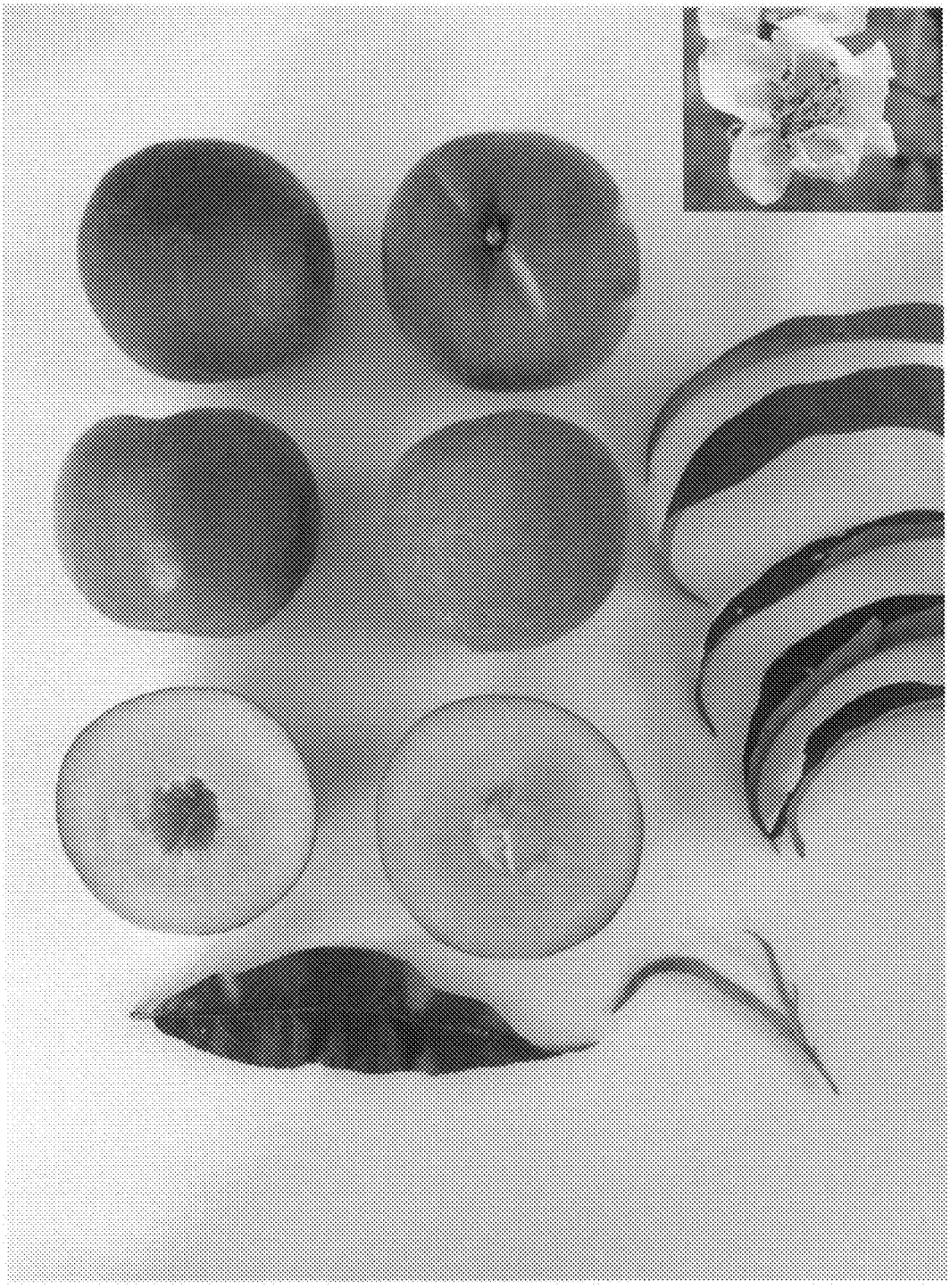

* * * * *